United States Patent [19] 4,109,005
Lunsford et al. [45] Aug. 22, 1978

[54] METHOD OF INCREASING RATE OF GASTRIC EMPTYING WITH PYRROLIDINYLBENZAMIDES

[75] Inventors: Carl D. Lunsford; Reevis S. Alphin, both of Richmond, Va.

[73] Assignee: A. H. Robins Company, Inc., Richmond, Va.

[21] Appl. No.: 795,827

[22] Filed: May 11, 1977

[51] Int. Cl.² ............................................. A61K 31/40
[52] U.S. Cl. ................................................... 424/274
[58] Field of Search ......................................... 424/274

[56] References Cited

U.S. PATENT DOCUMENTS 3,177,252 4/1965 Thominet ........................ 260/559 S
3,963,745 6/1976 Duncan et al. ...................... 424/274

OTHER PUBLICATIONS

*The Merck Index*, Ninth Ed. (1976), Merck & Co., Inc., Rahway, N.J., pp. 801-802.

*Primary Examiner*—Frederick E. Waddell

[57] ABSTRACT

Pyrrolidinyl benzamides represented by the formula:

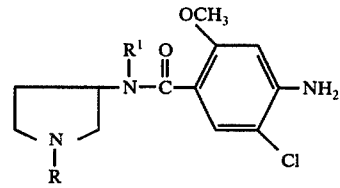

wherein R is methyl or cycloalkyl having 3 to 12 carbon atoms; R¹ is hydrogen or methyl and the pharmaceutically acceptable salts thereof are disclosed in methods which increase the rate of gastric emptying in mammals.

5 Claims, No Drawings

METHOD OF INCREASING RATE OF GASTRIC EMPTYING WITH PYRROLIDINYLBENZAMIDES

BACKGROUND OF THE INVENTION

1. FIELD OF INVENTION

The present invention relates to methods of increasing the rate of gastric emptying in mammals using pyrrolidinylbenzamides and is more particularly concerned with the use of certain 1-methyl and 1-cycloalkyl-3-pyrrolidinylbenzamides.

In certain individual mammalian subjects gastric motility is below normal, resulting in retention of stomach contents for extended periods of time. This may result in any one or more of a number of clinical symptoms such as reflux esophagitis, feelings of fullness with obvious signs of distension or ulceration.

2. DESCRIPTION OF THE PRIOR ART

The use of certain 1-substituted-3-pyrrolidinyl benzamides as anti-emetics have been disclosed in U.S. Pat. Nos. 3,963,745 and 3,966,957. Certain 1-benzyl-piperidinylbenzamides disclosed in Belgian Patent No. 826,994, including clebopride which is N-[4'-(1-benzyl)-piperidinyl]-2-methoxy-4-amino-5-chlorobenzamide, allegedly exhibit beneficial results in treatment of stomach disorders. Metoclopramide which is 4-amino-5-chloro-2-methoxy-N-[(2-diethyl-amino)ethyl]benzamide has been used to increase the rate of emptying of the stomach in mammals.

SUMMARY OF INVENTION

The present invention is concerned with methods and compositions for increasing the rate of gastric emptying in mammals used 1-substituted-3-pyrrolidinyl benzamides having the formula:

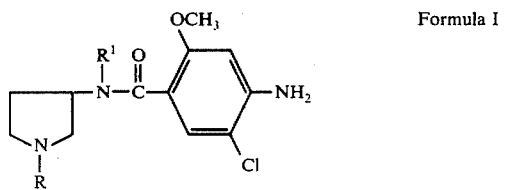

Formula I wherein;

R is methyl or cycloalkyl having 3–12 carbon atoms,
$R^1$ is hydrogen or methyl, and
the pharmaceutically acceptable addition salts thereof.

The compounds act to normalize gastric motility in mammalian subjects having otherwise too slow a rate of stomach emptying.

DESCRIPTION OF THE PREFERRED EMBODIMENTS

The compounds described hereinafter and represented by the foregoing Formula I have been shown by accepted pharmacological procedures to have utility in increasing the rate of gastric emptying in mammals.

Compounds for which positive increases in gastric emptying were demonstrated include the following.

| Example No. | Name of Compound |
|---|---|
| 1 | 4-Amino-5-chloro-2-methoxy-N-(1-methyl-3-Pyrrolidinyl)benzamide. |
| 2 | 4-Amino-5-chloro-2-methoxy-N-(1-cyclohexyl-3-pyrrolidinyl)benzamide fumarate. |
| 3 | 4-Amino-5-chloro-2-methoxy-N-(1-methyl-3-pyrrolidinyl)-N-methylbenzamide. |
| 4 | 4-Amino-5-chloro-2-methoxy-N-(1-cyclohexyl-3-pyrrolidinyl)-N-methylbenzamide disulfate monohydrate. |

The invention includes pharmaceutically acceptable acid addition salts which are formed with non-toxic organic and inorganic acids. Such salts are usually prepared by methods known to the art. The base is reacted with either the calculated amount of organic or inorganic acid in aqueous miscible solvent such as ethanol or isopropanol, with isolation of the salt by concentration and cooling or with an excess of the acid in an aqueous immiscible solvent, such as ethyl ether or isopropyl ether, with the desired salt separating directly. Exemplary of such organic salts are those with maleic, fumaric, benzoic, ascorbic, tartaric, malic and citric. Exemplary of inorganic salts are those with hydrochloric, hydrobromic, sulfuric, phosphoric and nitric acids.

Compounds of Formula I also exhibit anti-ulcer activity which ideally complements the activity of increased rate of gastric emptying.

It is, accordingly, an object of the present invention to provide a method for increasing the rate of gastric emptying in mammals. A further object is to provide methods which ameliorate gastric ulceration. Additional objects of the invention will become apparent to those skilled in the art to which this invention pertains.

The compounds useful in the method of this invention are disclosed in or can be prepared by the procedure of U.S. Pat. Nos. 3,963,745 and 3,966,957.

The term "cycloalkyl" as used herein includes primarily cyclic radicals containing 3 to 12 carbon atoms inclusive and encompasses such groups as cyclopropyl, cyclobutyl, cyclopentyl, cyclohexyl, methylcyclohexyl, propyl cyclohexyl, cycloheptyl, cyclooctyl and cyclodecyl.

Gastric emptying activity of the compounds of the present invention was demonstrated using the following procedure. Female Sprague-Dawley rats weighing 117–221 g. were starved 24 hours in individual screen-bottom cages with water ad libitum. Animals were arranged in groups of eight. At time 0, the compounds were administered intraperitoneally to the rats at 9 mg/kg. in 5% acacia (0.4 ml/100 g. body weight). The control group was dosed with acacia alone, 4 ml/kg intraperitoneally. Thirty minutes following dosing, the rats were given orally, by stomach tube, 3 ml. of a test meal consisting of methylcellulose base to which had been added beef bouillon, casein, powdered sugar and corn starch to yield a semi-solid homogenous paste. 60 minutes following the test meal (ninety minutes total time), rats were sacrificed by cervical dislocation, laparotomized and the stomachs removed. The full stomachs were weighed on an analytical balance after which they were cut open, rinsed and the empty stomach weighed. The difference between full and empty stomach weights represents the amount of meal remaining in the stomach and was subtracted from the weight of 3.0 ml. of test meal to yield the amount of meal emptied from the stomach during the test period. Table 1 summarizes test results of certain compounds of the present invention and metoclopramide.

Table 1
Effect of Compounds of Formula I on Gastric Emptying in Rats

| Compound Example No. | R | R¹ | % Change in Gastric Emptying (60 minutes after test meal) (a) | Significance p-Value (e) |
|---|---|---|---|---|
| 1 (b) | CH₃ | H | +41 | <0.005 |
| 2 (c) | C₆H₁₁ | H | +60 | <0.001 |
| 3 | CH₃ | CH₃ | +36 | <0.05 |
| 4 (d) | C₆H₁₁ | CH₃ | +14 | >0.05 |
| Metoclopramide | | | +60 | <0.001 |

(a) Average of 8 animals each compound. 9 mg/kg. of each compound administered, i.p. at 0 time. Animals were given test meal 30 minutes after compound administration and amount emptied determined 60 minutes after test meal given.
(b) Hydrochloride salt.
(c) Fumarate salt.
(d) Oxalate hemihydrate salt.
(e) Statistical analysis by Student t-test.

The compound of Example 2 was further evaluated in dose response at 0.33, 1.00, 3.00 and 9.00 mg/kg., i.p., in 5% acacia. The results are summarized in Table 2.

Table 2
Dose Response on Gastric Emptying In Rats Using 4-Amino-5-chloro-2-methoxy-N-(1-cyclohexyl-3-pyrrolidinyl)-benzamide Fumarate.

| Dose(a) mg/kg, i.p. | No. of Rats | % change(b) Meal Emptied | Significance p-Value (c) |
|---|---|---|---|
| 0.33 | 15 | +18 | p<0.01 |
| 1.00 | 16 | +36 | p<0.001 |
| 3.00 | 15 | +49 | p<0.001 |
| 9.00 | 16 | +60 | p<0.001 |
| None (control) (5% acacia 4 ml/kg) | 90 | | |

(a)Compound dose at 0 time.
(b)Rats dosed orally 30 minutes after compound dose with 3.0 ml. of test meal. Gastric emptying determined 60 minutes after test meal dose compared to controls.
(c) Statistical analysis by "Student t-test."

The compound (Example 2) also reduced ulceration in the pyloric-ligated rat as demonstrated using the following procedure.

GASTRIC ANTIULCER PROCEDURE

Female Sprague-Dawley rats weighing 114-150 g. were starved 48 hours in individual screen-bottom cages with water ad libitum. Animals were arranged into groups of six rats each. Rats were injected subcutaneously at the time of pyloric-ligation and again 6 hours later. Nineteen hours after ligation, rates were sacrificed, their stomachs removed and cut open, rinsed under water and placed flat on cardboard sheets. The compound of Example 2 and metoclopramide were tested at doses of 3.0, 9.0 and 27.0 mg/kg. in 5% acacia. Rats dosed with 5% acacia served as controls. Stomachs were evaluated for ulcer formation using an arbitrary grading system (ulcer index) which took into consideration both the incidence as well as severity of ulceration. Maximum ulceration is graded as 200 points, death and performation being awarded 20 points each. Statistical analysis was performed by using the "Student t-test" for significance. Results are in Table 3.

Table 3
Gastric Antiulcer Comparison In Rats

| Compound | Dose(a) mg/kg s.c. | No. of Rats | Ulcer(b) Index ±S.E. | % Change | Significance p-Value |
|---|---|---|---|---|---|
| Example 2 | 3.0 | 12 | 102 ± 13 | −17 | >0.05 |
| | 9.0 | 12 | 100 ± 18 | −18 | >0.05 |
| | 27.0 | 12 | 68 ± 13 | −44 | <0.05 |
| Metoclopramide | 3.0 | 11 | 124 ± 22 | + 2 | >0.05 |
| | 9.0 | 12 | 90 ± 13 | −26 | >0.05 |
| | 27.0 | 10 | 115 ± 22 | − 6 | >0.05 |
| None (Control) 2 mg/kg | | 11 | 122 ± 21 | — | — |
| (5% acacia) | | | | | |

(a)This dose given subcutaneously at time of pyloricligation and again after 6 hours.
(b)19 Hours after ligation and first dose.

The pharmaceutical compositions used in this invention are comprised of compounds of Formula I above in an amount sufficient to increase the rate of gastric emptying in mammalian subjects having too slow a rate of emptying. The compositions contain 5 to 25 mg. per dose which, administered three times per day, usually brings about the desired effect.

The pharmaceutical carrier employed in the composition can be either solid or liquid. When the compositions are administered orally, which is the preferred route, solid carriers are chosen from such as lactose, magnesium or aluminum stearate, terra alba, sucrose, talc, stearic acid, gelatin, agar, and pectin acacia. Exemplary of carriers for oral administration are vegetable oils and water. When route of administration is parenteral, water is an ideal carrier.

A wide variety of pharmaceutical forms can be employed by methods well known to the art. Thus, if a solid carrier is used, the composition can be tableted or prepared as a powder, a troche, a lozenge, or a suppository. Gelatin capsules containing the medicament can also be prepared. If a liquid carrier is used, the composition can be in the form of a soft gelatin capsule, a liquid suspension, or a syrup. Parenteral dosage forms are obtained by dissolving a water-soluble salt of the compounds of Formula I in water or saline solution in a concentration such that 1 cc. of the solution contains from 1.0 mg. to 25 mg. of active agent. The solution can then be filled into single or multiple dose ampoules.

The method in accordance with this invention comprises administering internally to warm blooded animals, including humans, certain N-(1-substituted-3-pyrrolidinyl)benzamides or a non-toxic organic or inorganic acid addition salt thereof, preferably with a non-toxic pharmaceutical carrier such as described above in an amount to bring about normalization of stomach emptying in mammalian subjects wherein stomach emptying is too slow. The active agent which increases the rate of gastric emptying is administered orally or parenterally in repeated doses as determined by trial and error until a satisfactory result in obtained.

What is claimed is:

1. The method of increasing the rate of gastric emptying in mammalian subjects which comprises administering orally or parenterally thereto an effective amount of compounds selected from those having the formula:

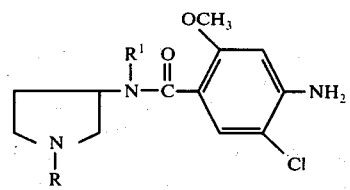

wherein;
R is methyl or cyclohexyl having 3-12 carbon atoms,
R¹ is hydrogen or methyl, and
the pharmaceutically acceptable salts thereof.

2. The method of claim 1 wherein the compound is 4-amino-5-chloro-2-methoxy-N-(1-methyl-3-pyrrolidinyl)benzamide.

3. The method of claim 1 wherein the compound is 4-amino-5-chloro-2-methoxy-N-(1-cyclohexyl-3-pyrrolidinyl)benzamide fumarate.

4. The method of claim 1 wherein the compound is 4-amino-5-chloro-2-methoxy-N-(1-methyl-3-pyrrolidinyl)-N-methylbenzamide.

5. The method of claim 1 wherein the compound is 4-amino-5-chloro-2-methoxy-N-(1-cyclohexyl-3-pyrrolidinyl)-N-methylbenzamide disulfate monohydrate.

* * * * *